United States Patent [19]

Sigl et al.

[11] 4,049,764
[45] Sept. 20, 1977

[54] METHOD OF FORMING HIGHLY ABSORBENT FILAMENTS AND WEBS HAVING IMPROVED SOFTNESS, WICKING, AND SOLVENT DRYING CHARACTERISTICS

[75] Inventors: Wayne C. Sigl, Black Creek; Frederick O. Lassen, Neehah, both of Wis.

[73] Assignee: Kimberly-Clark Corporation, Neeah, Wis.

[21] Appl. No.: 564,201

[22] Filed: Apr. 2, 1975

[51] Int. Cl.² .................................................. D01D 5/08
[52] U.S. Cl. .................................. 264/178 F; 106/170; 106/187; 106/189; 264/187; 536/62; 536/56; 536/58
[58] Field of Search .............................. 264/200, 187; 260/17.4 CL, 219; 162/157 R; 428/393; 536/62, 56, 58, 84; 106/170, 187, 189, 198

[56] References Cited

U.S. PATENT DOCUMENTS

| | | | |
|---|---|---|---|
| 1,896,725 | 2/1933 | Tanner | 260/219 |
| 3,366,582 | 1/1968 | Adams et al. | 260/17.4 GC |
| 3,482,011 | 12/1969 | Bohrer | 264/207 |
| 3,565,886 | 2/1971 | Clermont | 260/219 |
| 3,658,790 | 4/1972 | Bernardin | 260/219 |
| 3,691,154 | 9/1972 | Bernardin | 260/219 |
| 3,739,782 | 6/1973 | Bernardin | 260/219 |
| 3,740,940 | 6/1973 | Berkovitch | 57/140 R |
| 3,785,918 | 1/1974 | Kawai et al. | 264/188 |
| 3,914,354 | 10/1975 | Ueki et al. | 264/211 |
| 3,952,081 | 4/1976 | Epstein et al. | 264/211 |

*Primary Examiner*—Jay H. Woo
*Attorney, Agent, or Firm*—Daniel J. Hanlon, Jr.; William D. Herrick; Raymond J. Miller

[57] ABSTRACT

In the formation of highly absorbent and rapidly wicking filaments and web structures by extrusion and solvent drying of extrudates composed of highly swollen hydrophilic chemically modified cellulose fibers, improved results are obtained in the form of a softer and better wicking product by treatment of the extrudate prior to extrusion. The extrudate is a mass containing the swollen chemically modified cellulose fibers and a water content of up to 98% at the time of extrusion. By adding to the extrudate, prior to extrusion, an amount of from about 2 to 50% of the solvent to be used in drying in the form of pure solvent or in the form of a mixture containing solvent but which may contain water or other non-solvent and the solvent to be used in drying, a much better performing extrudate is produced which results in better filament formation, improved bonding between filaments, lower water content in the extrudate, faster drying of the extruded product, and a softer, better wicking product.

7 Claims, 5 Drawing Figures

| EX. NO. | EXTRUDATE DATA ||| | WEB DATA |||||||||
|---|---|---|---|---|---|---|---|---|---|---|---|---|
| | %(W/W) SWELLING MEDIA | %(W/W) H₂O | %(W/W) SOLVENT | DRYING SOLVENT | 1000 G (g LIQ./g FIBER) RETENT. || AVE. WEB WT. GRAMS/IN.² | WICKING TIME IN MINUTES || BONDING TYPE | THICKNESS AT 0 P.S.I. IN INCHES | HAND | SURFACE FEEL |
| | | | | | H₂O | NORMAL SALINE | | H₂O | SAL | | | | |
| 1 | 93.5 | 93.5 | 0.0 | ACETONE | 12.65 | 4.63 | 0.41 | 0.83 | 0.38 | VERY WEAK CONTACT | 0.142 | STIFF | HARSH |
| 2 | 95.7 | 95.7 | 0.0 | ACETONE | 11.19 | 4.49 | 0.28 | 0.49 | 0.23 | CONTACT-FUSED CROSS | 0.084 | GOOD FLEXIBILITY | MEDIUM |
| 3 | 94.7 | 90.9 | 3.8 ACETONE | ACETONE | 11.93 | 4.95 | 0.30 | 0.85 | 0.22 | CONTACT-FUSED CROSS | 0.081 | GOOD FLEXIBILITY | MEDIUM |
| 4 | 94.8 | 75.8 | 19.0 ACETONE | ACETONE | 9.83 | 4.04 | 0.35 | 1.49 | 0.30 | CONTACT-FUSED CROSS | 0.094 | SLIGHTLY STIFF | MEDIUM TO SLIGHTLY HARSH |
| 5 | 94.7 | 90.9 | 3.8 ISOPROPANOL | ACETONE | 11.00 | 4.73 | 0.28 | 0.88 | 0.26 | CONTACT-FUSED CROSS | 0.093 | VERY GOOD FLEXIBILITY | MEDIUM |
| 6 | 94.7 | 90.9 | 3.8 ISOPROPANOL | 99% ANHY. ISOPROPANOL | 11.30 | 5.02 | 0.30 | 0.43 | 0.35 | CONTACT-FUSED CROSS | 0.091 | VERY GOOD | SMOOTH, SOFT |
| 7 | 97.6 | 97.6 | 0.0 | ACETONE | 43.46 | 21.86 | 0.02 | — | 2.97 | VERY WEAK FUSED | 0.030 | VERY GOOD | SMOOTH SOFT |
| 8 | 96.6 | 73.6 | 23.0 ACETONE | ACETONE | 32.60 | 14.21 | 0.03 | — | 2.09 | STRONG FUSED | 0.075 | VERY GOOD | SMOOTH SOFT |

FIG. 5

METHOD OF FORMING HIGHLY ABSORBENT FILAMENTS AND WEBS HAVING IMPROVED SOFTNESS, WICKING, AND SOLVENT DRYING CHARACTERISTICS

BACKGROUND OF THE INVENTION

1. Field of the Invention

This invention relates to highly absorbent filaments and webs as well as methods for making them. More specifically, it pertains to improvements having general utility in processes for solvent drying fibrous materials such as the method described in copending and co-assigned U.S. patent application Ser. No. 402,311 to Lassen entitled "Filaments of Chemically Modified Cellulose Fibers, Method of Making Such Filaments and Webs and Products Produced Therefrom" filed Oct. 1, 1973. As described therein, filaments of chemically modified cellulose fibers and webs constructed from such filaments that exhibit, for aqueous systems, high absorbency and wicking properties which can be controlled and varied from slow to very fast are produced by extrusion of chemically modified cellulose fibers and solvent drying. Such filaments and webs are particularly suitable for applications where it is desirable to draw a liquid away from a surface and concentrate it in a particular layer or location. These applications include, by way of example and not limitation, disposable diapers, sanitary napkins, wipes, surgical sponges and the like.

2. Description of the Prior Art

The chemical modification of cellulose to increase its absorbency has been previously described and can be considered in a broad sense to fall into three major classifications in terms of methods:
 a. Chemical substitution, etherization, or esterification;
 b. Chemical substitution plus cross-linking; and
 c. Polymeric grafting.

For example, U.S. Pat. No. 3,670,069 to Mitchell is directed to absorbent fibers formed by extruding solutions such as those prepared from a hydroxyalkyl cellulose. As examples of category a above, Bernardin U.S. Pat. Nos. 3,658,790; 3,691,154; and 3,739,782 disclose absorbent fibers and batt-like mats formed from phosphorylated cellulose or its acid form and products incorporating them. An example of category b above is U.S. Pat. No. 3,589,364 to Dean et al which discloses absorbent structures including crosslinked fibers of carboxymethylcellulose and products made therefrom. Category c above is exemplified by the formation of acrylonitrile grafted cellulose absorbent fibers and products as disclosed in U.S. Pat. Nos. 3,194,727 to Adams et al; 3,455,643 to Gruber et al; 3,065,041 to Soon; and 3,046,078 to Salsbury.

The above-mentioned Lassen patent application describes the formation of absorbent and highly wicking web and filament structures by extrusion and solvent drying of extrudates composed of highly swollen, hydrophilic, chemically modified cellulose fibers such as, phosphorylated pulp fibers or carboxymethylcellulose fibers. Extrusion into a solvent bath results in rapid drying of the fibers forming soft, highly wicking filaments which can be collected to form a web. In web formation various degrees and types of bonding may be obtained, depending, in part, upon the particular conditions of drying.

SUMMARY OF THE INVENTION

The present invention relates particularly to improvements in processes of forming highly absorbent webs and filament structures by extrusion and solvent drying. In producing filaments and webs by the method described in the above-referenced Lassen application, for example, it has been considered necessary to maintain the consistency of the extrudate within a range narrowly defined by the degree of swelling of the fibers making up that extrudate in order to obtain the best combination of filament or web properties. Extrusion of an extrudate having too low a water content for the degree of fiber swelling present results in a material having, after solvent drying, an undesirable degree of harshness and stringiness. Extrusion of an extrudate having too high a water content for the degree of fiber swelling, on the other hand, tends to produce a weak, flat filament having poor wicking properties. This requirement, in practice, has proven difficult to satisfy on a continuous, high production basis.

In accordance with the present invention, the necessity for operating within this narrow consistency range is avoided by treatment of the extrudate with a minor amount of a solvent prior to extrusion and solvent drying.

DESCRIPTION OF THE PREFERRED EMBODIMENTS

In order to insure a complete understanding of the present invention, the intended meaning of certain terms used in the description will now be stated:

"Chemically modified cellulose" refers to cellulosic materials, the composition and/or structures of which have been transformed by derivatization in such a way as to induce a significant increase in their hydrophilic character. Examples of derivatization processes include carboxylation, phosphorylation, and grafting of acrylic segments. The term does not include cellulosic solutions or other cellulosic compositions in which the individual fibers or other basic structures, themselves, lose their identities.

"Highly absorbent" as used herein indicates that the modified cellulose will absorb significantly more of the liquid being used than will unmodified cellulose under the same conditions. It is recognized that the particular absorbency rating will depend not only on the specific material tested but on the conditions under which measurements are made. For example, the absorbency of a material under pressure may be quite different from an absorbency in an uncompressed state. "Fiber" is used herein in reference to the fibers of chemically modified cellulose that are formed into filaments by extrusion; for cost considerations they have a length preferably of about papermaking fiber size, e.g., about 0.146 inch and a diameter preferably of about 0.002 to 0.003 inch, although larger fibers such as cotton linters may be used. "Filaments" as used herein means elongated strands composed of interbonded, generally aligned fibers.

"Extrudate" refers to a mass of extrudable, hydrophilic, fibrous cellulosic material which has been swollen by the inhibition of a solvent to such an extent as to plasticize the individual cellulosic fibers and render them independently mobile.

"Contact bond" is defined as a surface bond formed between filaments at locations where they touch; the integrity and alignment of each filament is substantially maintained in the bond areas and upon the application of tensile forces to the web, breaking preferentially occurs in the bond areas.

"Fused bond" is defined as a bond formed between filaments wherein they become welded or merged together in the bond area; the bond mass is integral and will not break any more readily than the filaments, themselves.

"Consistency" as used herein means weight percent swelling medium in any of the compositions or mixtures recited here, and all percentages are by weight unless otherwise noted.

The present invention finds its particular utility in processes using chemically modified cellulose as further described in the above-mentioned Lassen patent application Ser. No. 402,311. Specifically, that portion of the Lassen application describing the preparation of chemically modified cellulose fibers and the production of filaments therefrom is incorporated herein by reference. Thus, whether such fibers are phosphorylated by the process described in the Lassen application or obtained commercially in a form marketed, for example, as Buckeye brand carboxymethyl cellulose fibers by Buckeye Corporation, they may be utilized in accordance with the present invention so long as they form an extrudable mass without dissolving to the extent that the fibers become indistinguishable.

To form the extrudate, water is added to the chemically modified cellulose fibers until a highly swollen, gel-like mass is formed. It has been found that the degree of swelling is a reliable indicator of the extrudability of the extrudate. This desirable degree of swelling may be determined by the 1000 g. test as described in the above recited Lassen application. Generally the desirable extrudates will have a water content of from about 50 to 98% and preferably 80 to 92% by weight. However, it is to be emphasized that the swollen nature of the fibers is a more important factor to be considered in extrudability than is the specific water content.

In accordance with the present invention, an extrudate is formed having a water content 1 to 6% lower than the desired spinning consistency, and it is treated with a solvent or solvent mixture. The selection of a solvent for use in this treatment will depend upon factors such as the degree of softness and wicking properties desired as well as cost, recoverability, and other process parameters. Preferably, however, the solvent used in the treatment mixture is the same solvent used for solvent drying the extruded filaments. Examples of solvents which can be used in the mixture include acetone, propanol, isopropanol, butanol, methanol, ethanol and other polar solvents in general which are soluble in water. The treatment of the extrudate is effected by mixing into the fiber mass an amount of solvent in the range of from about 2 to about 50% by weight based on the total weight of final extrudate. The solvent may be mixed in pure or diluted with up to about 90% by volume of a nonsolvent such as water. The combination must be thoroughly mixed in order to prevent premature solvent drying of the extrudate which renders the material much more difficult to extrude. The period of treatment may be in the range of from about 3 to 10 minutes depending upon the type of mixing used, and the solvent mixture is preferably integrated into the extrudate through the use of mechanical mixers such as a Hobart Mixer Model #M-50.

After this treatment the extrudate is preferably extruded promptly into a solvent bath and dried in the manner described in detail in the above-referenced Lassen application. Thus, the extruded product is directed into a solvent bath for a period of time depending upon the quantity of water to be removed, filament size and desired properties. For example, in an acetone solvent drying system, preferably the dried fibers contain less than 10% water, in which case contact with the solvent bath for at least about 15 to 60 seconds is usually sufficient. When a single solvent bath such as acetone is used, it is preferably less than 10% water by weight.

Webs may be formed by combining the filaments prior to the drying step by directing them onto a moving screen which, in turn, carries the web into the solvent bath. Particularly when a solvent such as acetone is utilized, interfilamentary bonds will be formed wherever filament crossings occur. While the nature of these bonds is not fully understood, it is believed that the type of bond formed depends upon the degree of plasticization or swelling of the individual fibers and/or the degree of surface drying occurring prior to filament contact as described in greater detail in the above-identified Lassen application. Fused bonds, therefore, will be formed between filaments composed of highly swollen and/or plasticized fibers while contact bonds will be formed between those which are composed of fibers that are lower in consistency or are in a less swollen and/or less plasticized form. In any event, the bonding obtained in accordance with the process as described is quite adequate to form a self-sustaining web with sufficient integrity to withstand further handling and processing without disintegration. For faster wicking webs contact bonds are preferred.

The invention will now be described in connection with specific preferred embodiments, but it is to be understood that it is not intended to limit the invention to those embodiments. On the contrary, it is intended to cover all alternatives, modifications, and equivalents as may be included within the spirit and broad scope of the invention as defined by the appended claims.

EXAMPLE 1

An extrudate of swollen phosphorylated cellulose was prepared in the following manner. 2,383g (bone-dry) of Northern spruce pulpboards were soaked for 5 minutes at 50° C in a solution of 47% urea, 23.5% orthophosphoric acid and 29.5% water by weight. Following this soaking the pulp was nipped using a commercial manually-powered washing machine wringer set at its highest nip pressure. The pressed pulp was then resoaked in the above solution for one-half minute and then renipped. Weighing of the pressed pulp showed it to have retained about 180% of its own weight of the solution. The pulp was then cured for 1 hour at 160°-170° C in a forced-draft oven. Following a water wash, the fibers were treated for one-half hour with 3.7% HCl(w/w) at 55°–65° C. Following another water wash, the fibers were soaked in 5.0% Na$_2$CO$_3$(w/w) for 1 hour. The fibers were removed from the base solution by centrifugation using a Sharples Model P-660 continuous centrifuge operating at a bowl speed of 5700 rpm, a conveyor differential of 16 rpm, a dam setting of No. 4, and an effluent flow rate of 10 liters/minute. The collected fibers were washed by slurrying them in water and recollected by centrifugation similar to above at an effluent flow rate of 8.0 liters/minute. Following reslurrying the collected fibers in water, the pH was adjusted to 7.2 using dilute HCl solution. Refining of the fibers was accomplished by the mechanical action of centrifuging the pulp from water slurries of about 2%(w/w) consistency 5 additional times. The centrifuge was operated at settings similar to above with the following respective effluent flow rates: 10 liters/min., 7.2 liters/min., 10 liters/min., 8 liters/min., and 4.5 liters/min. The final centrifugation yielded a stiff extrudate of phosphorylated pulp fibers containing 93.5%(w/w) H$_2$O.

Thirty milliliters of the above extrudate was extruded through an 18 gauge (I.D. $\approx$ 0.032 inch) syringe needle into a web-like structure 6 inches by 7 inches, solvent-dried in reagent-grade acetone, and the remaining solvent evaporated off. The average dried-down weight of the web was 0.41 g/sq. in. The resulting web was stiff and harsh feeling with very weak contact bonding.

EXAMPLE 2

A less-viscous extrudate was formed by mechanical mixing of additional water into the extrudate produced in Example 1 using a Hobart M-50 dough mixer. Water was added in the ratio of 150 mls. of water for each 375 g. of Example 1 extrudate. The resulting extrudate contained 95.7% water (w/w).

Thirty milliliters of this extrudate was extruded and solvent-dried in a manner similar to that of Example 1 to yield a web of an average weight of 0.28g/sq. in. The resulting web was more flexible and less harsh than that of Example 1, had similar 1000G retention values as that of Example 1, but had significantly faster wicking times that that for the web of Example 1. Unlike the web of Example 1, the resulting web showed significantly stronger bonding of both the contact and fused types.

Figure 2:
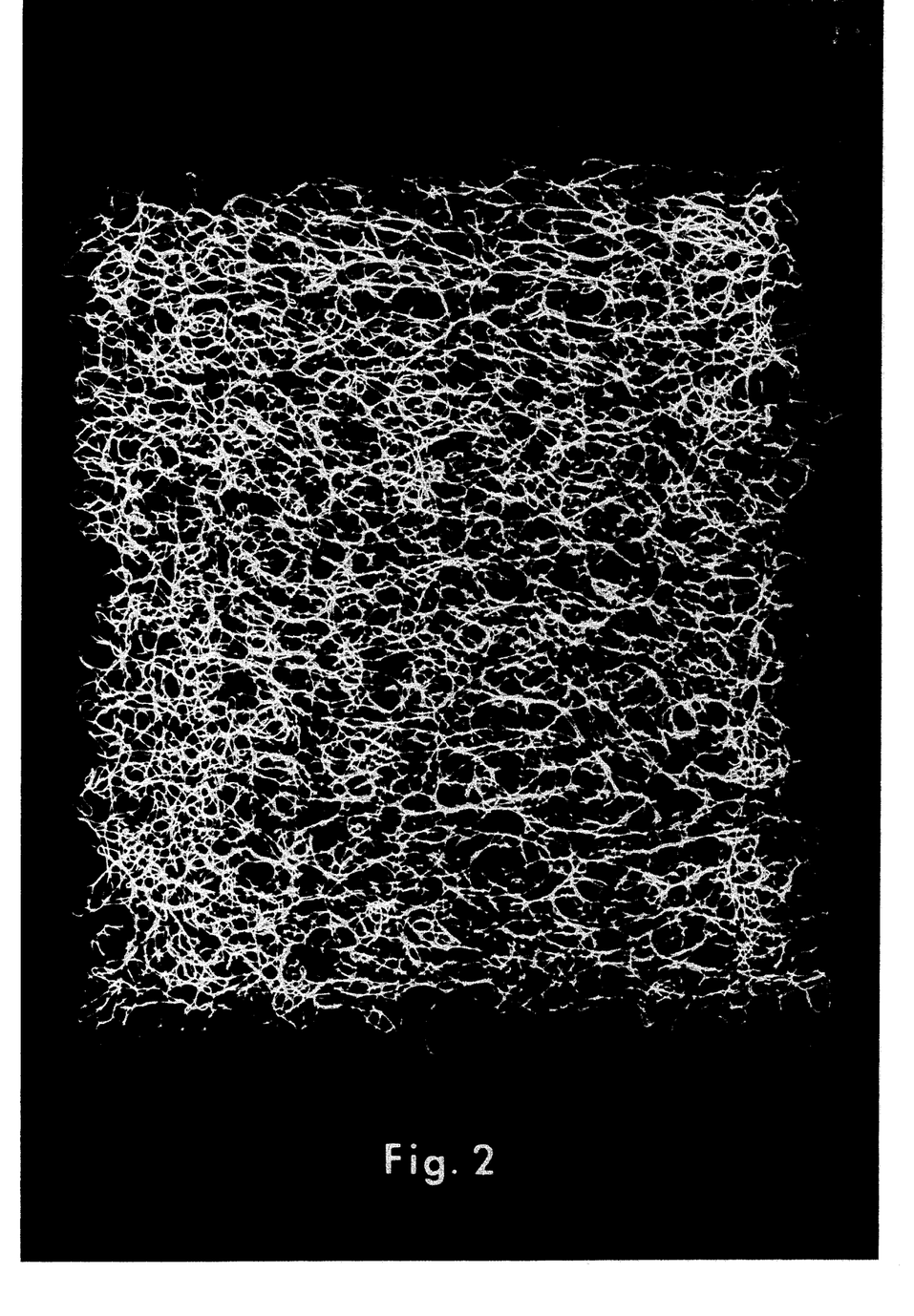
FIG. 2 is a photograph of phosphorylated pulp filament web formed in accordance with the present invention.

FIG. 2 is a photograph of a web produced as described in this Example, shown at actual size.

EXAMPLE 3

An extrudate was formed by mixing a solution of 20% acetone (by volume) in water into the extrudate of Example 1 in the ratio of 120 mls of solution for each 375g. of Example 1 extrudate. Mixing was accomplished using the Hobard M-50 dough mixer. The resulting extrudate had a consistency of 94.7(w/w), being 90.9%(w/w) H$_2$O and 3.8%(w/w) acetone.

Figure 3:
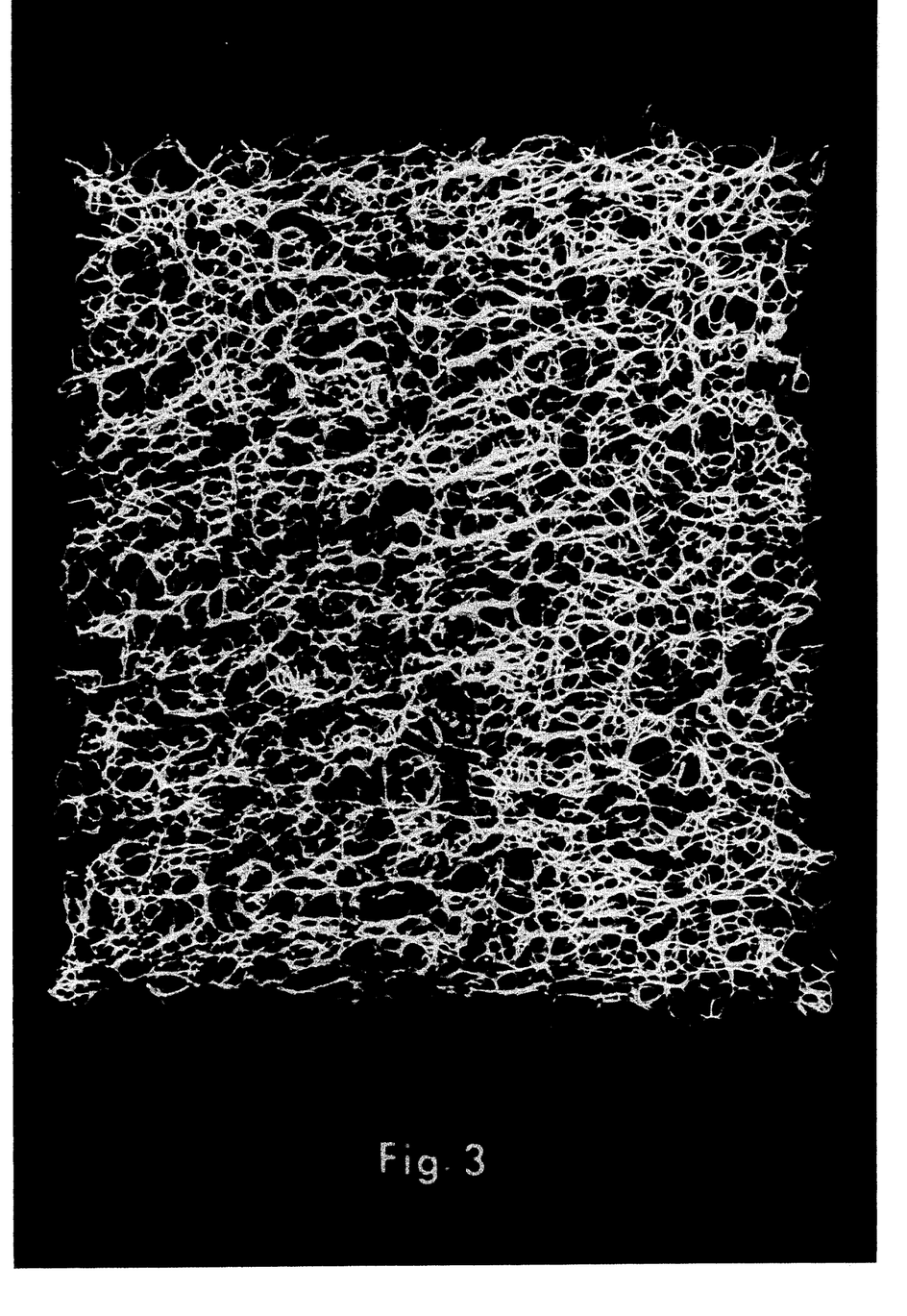
FIG. 3 is a photograph taken in the same manner as FIG. 2 of phosphorylated pulp filaments produced without the extrudate pre-treatment of the present invention.

Thirty milliliters of this extrudate was extruded and solvent-dried in acetone in a manner similar to that of the previous examples to yield a web of an average weight of 0.30g/sq. in. The characteristics of this web were comparable to those of the web of Example 2, except that bonding in this web was predominantly of the more desirable contact bonding type. FIG. 3 is a photograph of a web produced as described in this Example shown also at actual size, illustrating the increased bonding.

EXAMPLE 4

An extrudate was formed in a manner similar to Example 3 by mixing into the extrudate from Example 1 reagent-grade acetone until a good extrusion viscosity was obtained. Mixing again utilized the Hobart M-50 dough mixer, and the acetone was added slowly by spraying it into the mixing container with a syringe fitted with a 22 gauge (I.D. $\approx$ 0.22 inch) needle. A total of 100 mls. of acetone was added to 375 g. of the Example 1 extrudate, resulting in an extrudate that had a consistency of 94.8%, it being 78.5% H$_2$O and 19.0% acetone.

Thirty milliliters of the extrudate was extruded and solvent-dried in acetone in a manner simlar to the previous examples to yield a web of an average weight of 0.035 g/sq. in. The web had good hand and flexibility as well as good 1000G retention values. Bonding was again found to be predominantly the more desirable contact-bond type which, in turn, was accompanied by rapid saline wicking.

EXAMPLE 5

An extrudate was formed in the same manner as that used in Example 3 except that the solution mixed into the extrudate was 20% isopropanol (by volume) in water. Against 120 mls. of the solution was mixed into 375 g. of the Example 1 extrudate to yield a final extrudate having a consistency of 94.7%, being 90.9% water and 3.8% isopropanol.

A web was formed and acetone-dried using this extrudate in a manner similar to the examples above. The resulting web had an average weight of 0.28 g/sq. in., was very soft, and extremely white in color. It showed good 1000G retention values and again predominantly contact bonding. The saline wicking time was also very fast.

EXAMPLE 6

Thirty milliliters of the extrudate formed in Example 5 was extruded in a manner similar to that of the previous examples and was then solvent-dried for 1 minute in reagent-grade isopropanol. After removal from the solvent, the solvent adhering to the web was allowed to evaporate. The resulting web had an average weight of 0.30 g/sq. in., was extremely soft and white in color, and showed other characteristics similar to those of the web formed in Example 5.

EXAMPLE 7

An extrudate of swollen crosslinked carboxymethyl cellulose fibers was formed by obtaining Buckeye fibers and mixing water into them utilizing a Model M-50 Hobart dough mixer until a good extrusion consistency was obtained. The resulting extrudate was found to contain 97.6% water.

Thirty milliliters of this extrudate was extruded and solvent-dried in acetone to yield a web having an average web weight of 0.02 g./sq. in. This web was soft, white, and flexible, but was also found to be extremely fragile, disintegrating on only minor handling. Bonding was of the fused type.

EXAMPLE 8 an extrudate of crosslinked carboxymethyl cellulose fibers was made according to the present invention by obtaining Buckeye fibers and mixing into them in a Model M-50 Hobart mixer a solution that was 30% acetone (by volume) in water until a good extrusion consistency was reached. The resulting extrudate was found to have a consistency of 96.6%, being 73.6% water and 23% acetone.

Thirty milliliters of this extrudate was extruded and solvent-dried in acetone in a manner similar to the previous examples to yield a web of an average weight of 0.03 g./sq. in. The web was very soft, flexible, and white and, unlike the web of Example 7, was very strong. Bonding was of the fused type. Web characteristics were similar to those of the web of Example 7 except that the saline wicking time was significantly faster for this web than for the web of Example 7.

Figure 5:
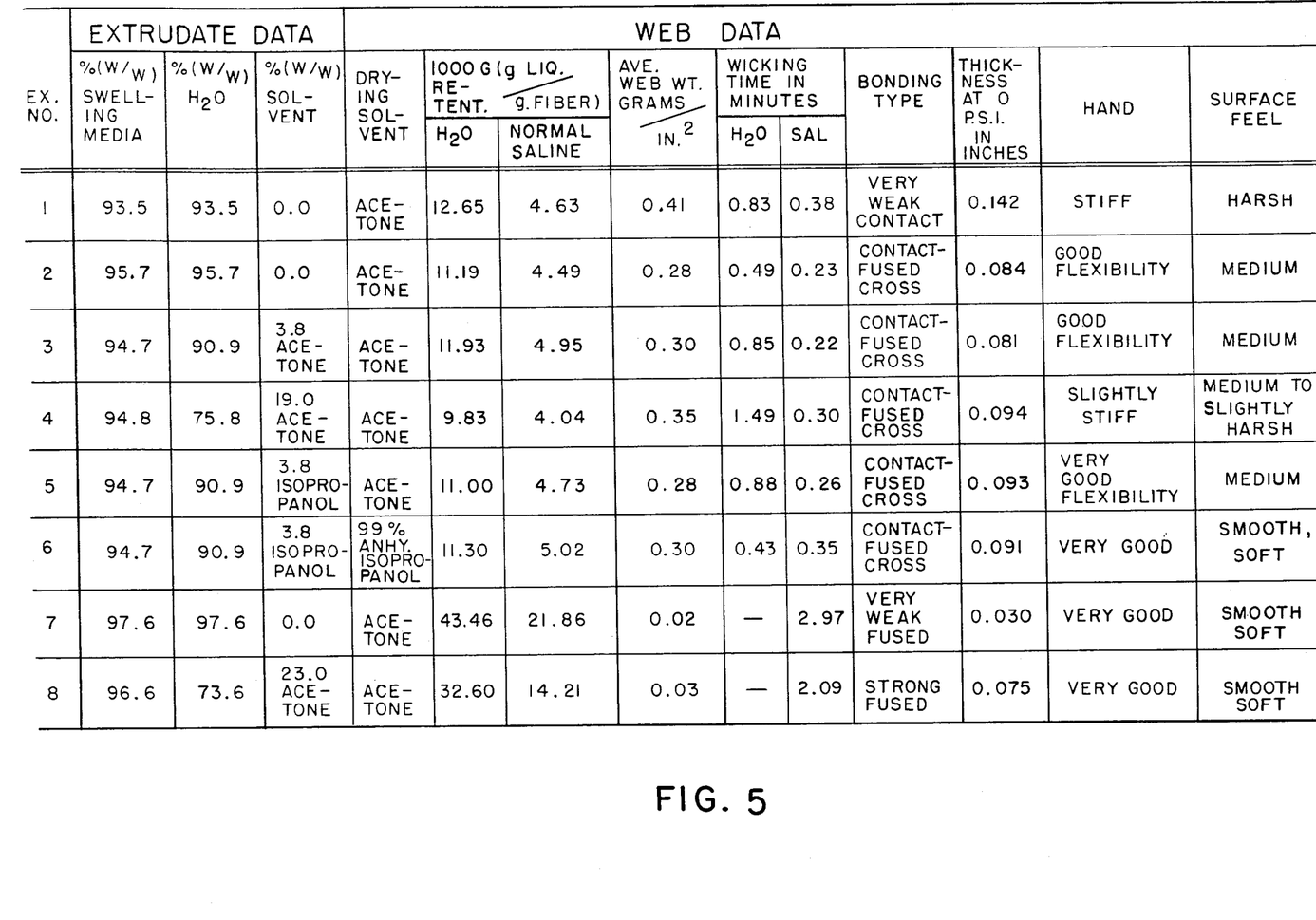
FIG. 5 is a table summarizing the examples.

FIG. 5 is a table that illustrates the improved filament and web properties obtained in accordance with the present invention. The results obtained were produced according to procedures as follows:

Water retention is defined in U.S. Pat. No. 3,670,069 to Mitchell et al at Col. 6, lines 51 to 70, as the moisture, expressed in terms of g. liquid per g. dry fiber, remaining in and on a rewet fiber specimen after it has been centrifuged for 10 minutes at an acceleration of 1000 times normal gravitational acceleration.

Wicking determinations were made as the test is described and illustrated in the above-mentioned Lassen application by supporting the web on concentric rings of conductive metal, applying water thereto, and measuring by means of electric current the time required for the water, or normal saline solution, to traverse the 1 1/16 inches between the rings.

Thickness measurements were made on a standard Model CS-55 C & S tester as supplied from Custom Scientific Instruments, Inc. Foot pressure applied was 0 p.s.i. over the weight of the foot, itself, during the test, and the pressure foot diameter was 1.129 inches. Results given are the average of at least five individual readings.

Other results are given in terms of subjective tests made by trained personnel.

While it is not desired to limit the invention to any particular theory, it is believed that the solvent contained within the swelled fiber extrudate limits the interfiber bonding during extrusion and subsequent solvent drying, thus reducing the tendency to produce harsh, string-like material. In turn, it permits the extrusion of the extrudate at lower water contents which would otherwise also tend to produce harsh, string-like material. Furthermore, such webs and filaments which would have otherwise tended to be slower wicking and have lower absorbency when produced by solvent drying alone have properties like those produced from extrudates having a consistency within the preferred range as described above. In addition, the present invention requires less solvent and increases the speed of drying with the result that higher productivity may be obtained. Thus, while the webs and filaments produced in accordance with the Lassen teachings are unique and have highly desirable absorbency and wicking properties, the improvement of the present invention reduces the sensitivity of the process in order to obtain its maximum benefits.

This objective is attained in accordance with the present invention by treating the extrudates of highly swollen chemically modified cellulose fibers with a solvent, preferably the solvent to be used in solvent drying. This pre-treatment produces an unexpected and highly beneficial improvement in the extrusion properties of the extrudate, making it much less sensitive to consistency and the swollen nature of the fibers. In addition to this important benefit, the pre-treatment results in a lower water content in the extrudate permitting greater economy in terms of ultimate drying costs and faster solvent drying of the extruded structures as well as producing the desired bonding between the filaments in web structures.

Figure 1:
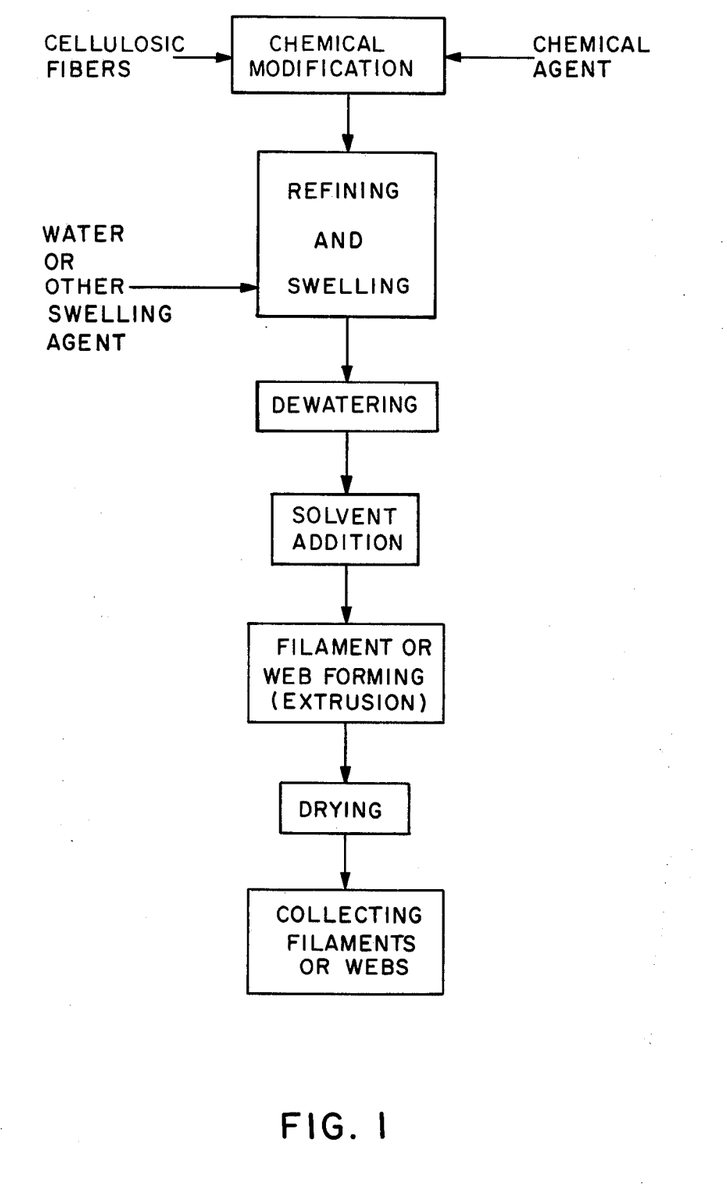
FIG. 1 is a flow diagram illustrating the process of the present invention.

As shown in FIG. 1, for example, the improvement of the present invention may be expressed in one embodiment as the fourth step of an overall process for web manufacture including chemical modification of cellulose fibers, refining/swelling, dewatering, solvent treatment, filament/web forming, drying, and filament/web collection.

FIGS. 2 and 3 illustrate webs formed utilizing comparative solvent amounts but utilizing the solvent treatment and without it, respectively. As can easily be seen, the web of the invention is more highly bonded with the bonds being of the desired contact type.

Figure 4:
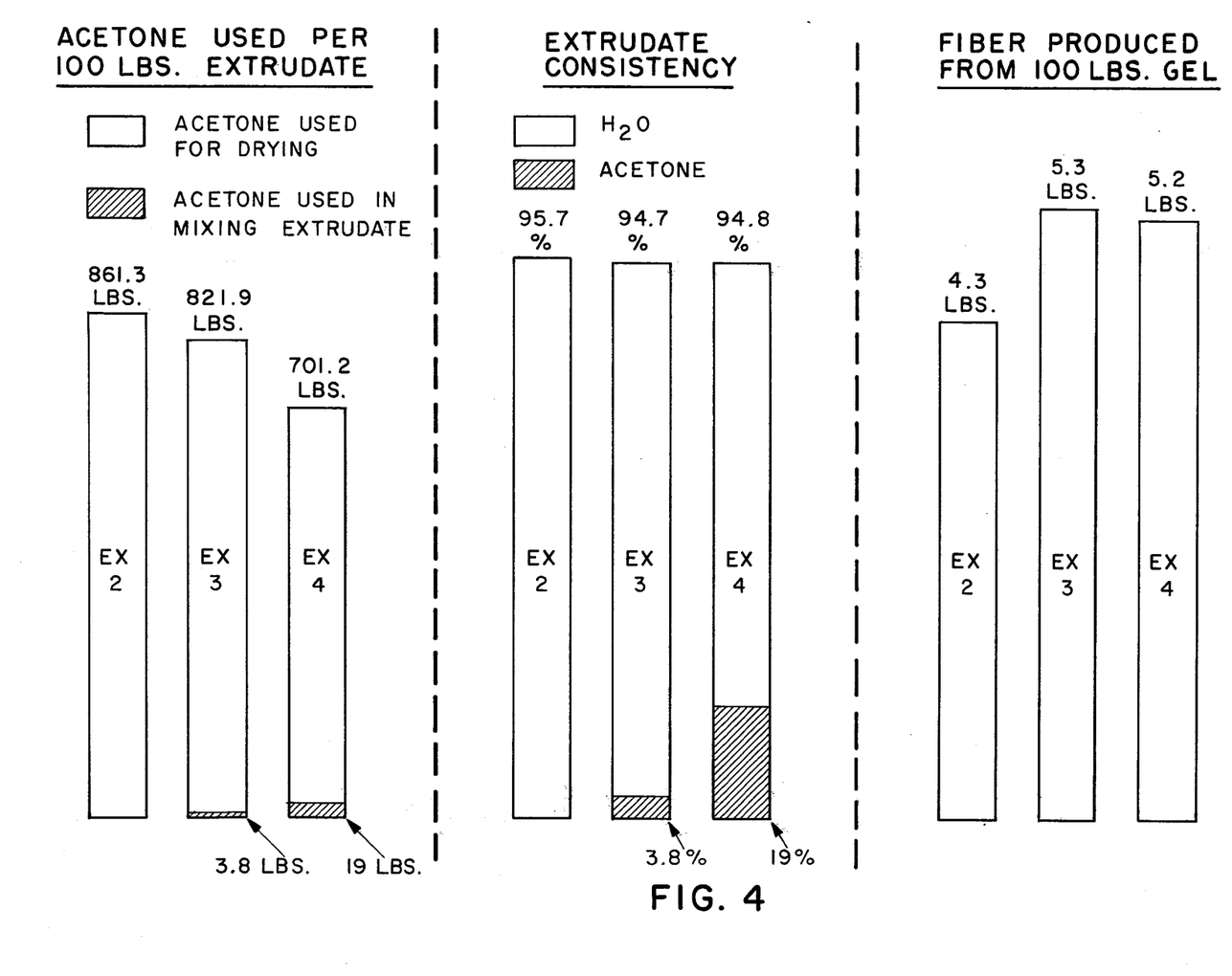
FIG. 4 is a graph illustrating the improvements in extrusion and solvent drying efficiencies resulting from the present invention.

FIG. 4 demonstrates the improved efficiencies obtained by means of the invention in terms of solvent used, extrudate consistency, and fiber produced. On a commercial scale it is apparent that the costs savings can be very significant.

Thus, it is apparent that there has been provided in accordance with the invention, an improved method of forming highly absorbent filaments and webs that fully satisfies the objects, aims and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

I claim:
1. In a method of producing filaments and webs of cellulose fibers, which have been transformed by derivitization to increase their hydrophilic character, by extrusion of said fibers from a plasticized fibrous extrudable mass including a swelling medium and solvent drying to remove the swelling medium,
   the improvement wherein about 2 to 50% of a polar solvent in the form of pure solvent for the swelling medium being removed by drying or a mixture containing the solvent and up to 90% of a non-solvent by volume is added to said extrudable mass and mixed for a period of from about three to about ten minutes prior to extrusion.
2. The method of claim 1 wherein said fibers are fibers of phosphorylated cellulose.
3. The method of claim 2 wherein said solvent is acetone and the same solvent is used for drying.
4. The method of claim 1 wherein said extrudable mass includes water and has a consistency 1 to 6% lower than the extrusion consistency and wherein said solvent is a polar solvent soluble in water.
5. A method of producing highly absorbent, rapid wicking filaments and webs including the steps of,
   1. chemically modifying cellulose fibers of papermaking size by
      a. chemical substitution, etherization, esterification;
      b. chemical substitution plus crosslinking; or
      c. polymeric grafting,
   2. forming an extrudable mass of said chemically modified cellulose fibers by adding water until said fibers are plasticized and independently mobile,

3. adding to said extrudable mass a polar solvent or solvent mixture which is soluble in water, in an amount of from 2 to 50% of the weight of water to be removed in drying;

4. mechanically mixing said solvent and extrudable mass for a period of from about 3 to 10 minutes; and 5. extruding said extrudable mass as filaments into a drying bath containing the remainder of said solvent.

6. The method of claim 5 including the additional step of collecting said extruded filaments to form a bonded web.

7. The method of claim 5 wherein said chemically treated fibers are phosphorylated cellulose and said solvent is acetone which is also used as the drying solvent.

* * * * *